Nov. 12, 1963 E. S. BOERNER Plant Pat. 2,303
ROSE PLANT
Filed Oct. 9, 1962
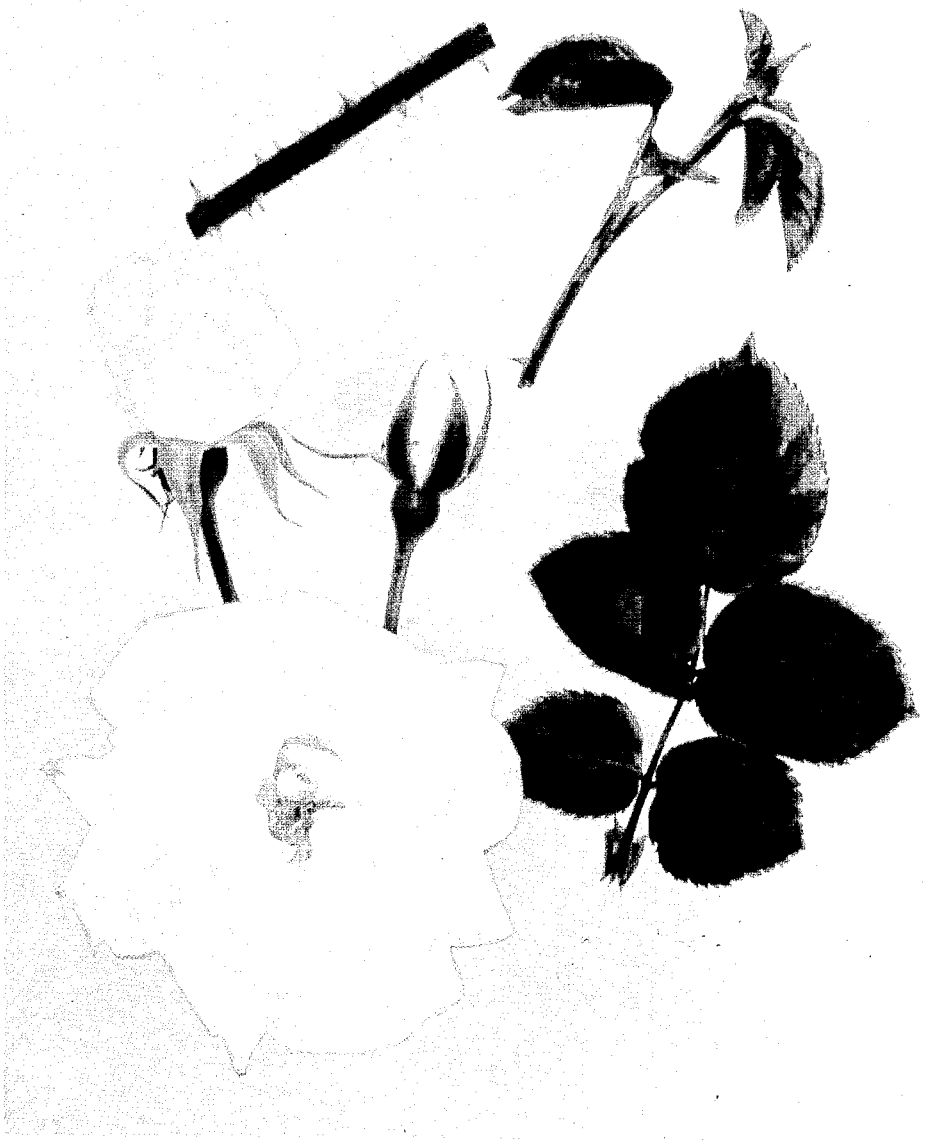
Inventor.
E. S. Boerner
By: Robb & Robb
Attorneys.

United States Patent Office

Plant Pat. 2,303
Patented Nov. 12, 1963

2,303
ROSE PLANT

Eugene S. Boerner, Newark, N.Y., assignor to Jackson & Perkins Company, Newark, N.Y., a corporation of New York Filed Oct. 9, 1962, Ser. No. 229,511
1 Claim. (Cl. Plt.—15)

The present invention relates to a new and distinct variety of rose plant of the hybrid tea class, which was originated by me by crossing an unnamed and unpatented seedling of "Diamond Jubilee" (Plant Patent No. 824) with the variety "Golden Masterpiece" (Plant Patent No. 1,284).

The primary objective of this breeding was to produce a new rose variety which bears flowers similar to those of "Diamond Jubilee," but which have a deeper color and at the same time retain the long-lasting qualities typical of "Diamond Jubilee" flowers. This objective was fully achieved, along with other desirable improvements, as evidenced by the following unique combination of characteristics which are outstanding in the new variety and which distinguish it from its parents, as well as from all other varieties of which I am aware:

(1) A medium tall habit of plant growth;
(2) A free blooming habit;
(3) A distinctive and attractive general color tonality of the flowers corresponding to Empire Yellow, lightly overcast with Light Cadmium;
(4) Good color retention of the flowers without fading to the very end; and
(5) Long-lasting qualities of the flowers similar to "Diamond Jubilee."

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Diamond Jubilee."
*Pollen parent.*—"Golden Masterpiece."
Classification:
*Botanic.*—Hybrid tea.
*Commercial.*—Hybrid tea.

*Flower*

(Observations made from specimens grown outdoors at Newark, New York, in the early morning during the early part of the month of July.)

Blooming habit: Recurrent—continuous; free.
Bud:
*Size.*—Large.
*Form.*—Ovoid; pointed; is not affected by wet or hot weather.
*Color.*—When sepals first divide—Cadmium Yellow, Plate 3. When petals begin to unfurl—Light Cadmium, Plate 4. When half-blown: inside of petals—Cadmium Yellow, Plate 3, lightly overcast with Light Cadmium, Plate 4; reverse of petals—Pinard Yellow, Plate 4, very lightly overcast with Apricot Yellow, Plate 4.
*Sepals.*—Slightly branched; curl back when petals begin to unfurl. Color: inside—Light Lumiere Green, Plate 17 in center, with edge of sepals Biscay Green, Plate 17; outside—Spinach Green, Plate 5, lightly overcast with Mikado Brown, Plate 29 on outer edge of sepals.
*Calyx.*—Color—Spinach Green, Plate 5. Shape—apple. Size—large. Aspect—smooth. Odor when rubbed—none.
*Peduncle.* — Length — medium. Aspect — prickly. Strength—erect; heavy. Color—Spinach Green, Plate 5, lightly overcast with Mikado Brown, Plate 29.
*Opening.*—Opens up well; is not affected by adverse weather conditions.
Bloom:
*Size.* — Medium. Average size when fully expanded—from 5 inches to 5½ inches.
*Borne.*—Both singly and several together.
*Stems.*—Medium length; strong.
*Form (when first open).*—Open-cupped. Permanance—retains its form to the end, but outer petals curl back.
*Petalage.*—Double (full but open center). Number of petals under normal conditions—from 30 to 35.
*Color.*—Center of flower—Empire Yellow, Plate 4, lightly overcast with Light Cadmium, Plate 4. Outer petals—Apricot Yellow, Plate 4. Base of petals (aiglet)—Lemon Chrome, Plate 4. Inside of petals—Empire Yellow, Plate 4. Reverse of petals—Baryta Yellow, Plate 4, very lightly overcast with Buff-Yellow, Plate 4. General tonality from a distance—Empire Yellow, Plate 4, lightly overcast with Light Cadmium, Plate 4.
*Discoloration.*—General tonality at end of first day—Empire Yellow, Plate 4, lightly overcast with Light Cadmium, Plate 4. Second day—Empire Yellow, Plate 4, lightly overcast with Light Cadmium, Plate 4. Third day—Empire Yellow, Plate 4, very lightly overcast with Light Cadmium, Plate 4.
Petals:
*Texture.*—Leathery; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; large.
*Persistence.*—Drop off cleanly.
*Fragrance.* — Moderate. Nature — tea (average hybrid tea scent).
*Lasting quality.*—On the plant—very long. As cut flower—long.

*Genital Organs*

Stamens, anthers: Large; many; regularly arranged around styles. Color—Deep Chrome, Plate 3.
Stamens, filaments (threads): Medium length. Color—Apricot Yellow, Plate 4.
Pollen: Color—Pale Yellow-Orange, Plate 3.
Styles: Bunched; uneven length; medium length; thin.
Stigmas: Color—Amber Yellow, Plate 16.
Ovaries: All enclosed in calyx.
Hips: None.
Seeds: None.

*Plant*

Form: Bush.
Growth: Vigorous; upright; medium tall; bushy.
Foliage: Compound of 3–5 leaflets.
*Size.*—Medium.
*Quantity.*—Normal.
*Color.*—New foliage; upper side—Yellowish Citrine, Plate 16, lightly overcast with Oxblood Red, Plate 1; under side—Van Dyke Red, Plate 13. Old foliage: upper side—Varley's Green, Plate 18; under side—Bice Green, Plate 17.

*Shape.*—Oval.

*Texture.* — Upper side — leathery; glossy. Under side—smooth.

*Ribs and veins.*—Ordinary.

*Edge.*—Serrated (saw-toothed).

*Serration.*—Both double and single; small.

*Leaf stem.*—Color—Garnet Brown, Plate 1. Under side—prickley.

*Stipules.*—Medium length; smooth.

Wood:

*New wood.*—Color—Oil Green, Plate 5, lightly overcast with Brazil Red, Plate 1. Bark—smooth.

*Old wood.* — Color — Forest Green, Plate 17. Bark—smooth.

Thorns:

*Thorns.*—Quantity: on main stalks from base—ordinary; on laterals from stalk—ordinary. Form—narrow base; medium length; some straight and some hooked downward. Color (when young)—Acajou Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a medium tall habit of plant growth, a free blooming habit, a distinctive and attractive general color tonality of the flowers corresponding to Empire Yellow, lightly overcast with Light Cadmium, good color retention of the flowers without fading to the very end, and long-lasting qualities of the flowers.

No references cited.